United States Patent
McFarlane

(10) Patent No.: US 7,011,314 B2
(45) Date of Patent: Mar. 14, 2006

(54) FLOATING SEAL ASSEMBLY FOR A TROCAR

(75) Inventor: Richard H. McFarlane, Singer Island, FL (US)

(73) Assignee: Taut, Inc., Geneva, IL (US)

( * ) Notice: Subject to any disclaimer, the term of this patent is extended or adjusted under 35 U.S.C. 154(b) by 0 days.

(21) Appl. No.: 10/424,564

(22) Filed: Apr. 28, 2003

(65) Prior Publication Data

US 2005/0261661 A1 Nov. 24, 2005

Related U.S. Application Data

(60) Provisional application No. 60/376,033, filed on Apr. 26, 2002.

(51) Int. Cl.
*F16J 15/00* (2006.01)
*A61M 5/00* (2006.01)
(52) U.S. Cl. ............... 277/626; 604/167.06; 604/256
(58) Field of Classification Search ........... 277/626, 277/644; 604/167.06, 256
See application file for complete search history.

(56) References Cited

U.S. PATENT DOCUMENTS

| | | |
|---|---|---|
| 3,313,299 A | 4/1967 | Spademan |
| 3,853,127 A | 12/1974 | Spademan |
| 3,989,049 A | 11/1976 | Yoon |
| 4,149,535 A | 4/1979 | Volder |
| 4,177,814 A | 12/1979 | Knepshield et al. |
| 4,351,328 A | 9/1982 | Bodai |
| 4,430,081 A | 2/1984 | Timmermans |
| 4,475,548 A | 10/1984 | Muto |
| 4,484,916 A * | 11/1984 | McPhee ............... 604/256 |
| 4,601,710 A | 7/1986 | Moll |
| 4,626,245 A | 12/1986 | Weinstein |
| 4,634,424 A | 1/1987 | O'Boyle |
| 4,654,030 A | 3/1987 | Moll et al. |
| 4,673,393 A | 6/1987 | Suzuki et al. |
| 4,715,360 A | 12/1987 | Akui et al. |
| 4,863,438 A | 9/1989 | Gauderer et al. |
| 4,895,565 A | 1/1990 | Hillstead |
| 4,902,280 A | 2/1990 | Lander |
| 4,917,668 A | 4/1990 | Haindl |

(Continued)

FOREIGN PATENT DOCUMENTS

WO      WO 98/50093      11/1998

OTHER PUBLICATIONS

U.S. District Court Web PACER (v2.4) Docket Report, Oct. 28, 2002, Applied Medical Reso v. US Surgical Corp.

*Primary Examiner*—Alison K. Pickard
(74) *Attorney, Agent, or Firm*—Malloy & Malloy, P.A.

(57) ABSTRACT

A seal assembly used in combination with a trocar assembly to maintain sealing engagement with the exterior surface of medical instrument, which may have different size diameters, introduced into the trocar assembly so as to maintain adequate insufflation pressure within a body cavity accessed by the trocar assembly. The seal assembly includes a seal member and is structured to permit free movement of the seal member at least radially within a chamber of a seal housing which may be attached to or part of the trocar housing. The seal member and the sealing chamber are cooperatively dimensioned to maintain at least the periphery of an outer surface of the seal member in surrounding relation to an inlet port of the chamber and thereby maintain seal engagement between corresponding interior surfaces of the chamber and the corresponding outer surfaces of the seal member.

15 Claims, 7 Drawing Sheets

U.S. PATENT DOCUMENTS

| | | |
|---|---|---|
| 4,931,042 A | 6/1990 | Holmes et al. |
| 4,978,341 A | 12/1990 | Niederhauser |
| 5,030,206 A | 7/1991 | Lander |
| 5,073,169 A | 12/1991 | Raiken |
| 5,104,383 A | 4/1992 | Shichman |
| 5,104,389 A | 4/1992 | Deem et al. |
| 5,108,380 A | 4/1992 | Herlitze et al. |
| 5,114,408 A * | 5/1992 | Fleischhaker et al. . 604/167.04 |
| 5,127,626 A | 7/1992 | Hilal et al. |
| 5,141,498 A | 8/1992 | Christian |
| 5,147,336 A | 9/1992 | Wendell et al. |
| 5,167,636 A | 12/1992 | Clement |
| 5,183,464 A | 2/1993 | Dubrul et al. |
| 5,197,955 A | 3/1993 | Stephens et al. |
| 5,205,831 A | 4/1993 | Ryan et al. |
| 5,207,656 A | 5/1993 | Kranys |
| 5,209,736 A | 5/1993 | Stephens et al. |
| 5,209,737 A | 5/1993 | Ritchart et al. |
| 5,211,633 A | 5/1993 | Stouder, Jr. |
| 5,242,409 A | 9/1993 | Buelna |
| 5,269,764 A | 12/1993 | Vetter et al. |
| 5,275,583 A | 1/1994 | Crainich |
| 5,299,813 A * | 4/1994 | McKenna .................... 277/422 |
| 5,300,036 A | 4/1994 | Mueller et al. |
| 5,308,336 A | 5/1994 | Hart et al. |
| 5,312,362 A | 5/1994 | Pfolsgraf et al. |
| 5,312,363 A | 5/1994 | Ryan et al. |
| 5,338,307 A | 8/1994 | Stephens et al. |
| 5,342,316 A * | 8/1994 | Wallace .................. 604/167.02 |
| 5,344,420 A | 9/1994 | Hilal et al. |
| 5,350,364 A | 9/1994 | Stephens et al. |
| 5,385,553 A * | 1/1995 | Hart et al. .............. 604/167.03 |
| 5,389,080 A | 2/1995 | Yoon |
| 5,389,081 A | 2/1995 | Castro |
| 5,391,153 A | 2/1995 | Haber et al. |
| 5,395,342 A | 3/1995 | Yoon |
| 5,397,335 A | 3/1995 | Gresl et al. |
| 5,401,248 A | 3/1995 | Bencini |
| 5,407,433 A | 4/1995 | Loomas |
| 5,411,483 A | 5/1995 | Loomas et al. |
| 5,429,598 A | 7/1995 | Waxman et al. |
| 5,429,609 A | 7/1995 | Yoon |
| 5,437,646 A | 8/1995 | Hunt et al. |
| 5,443,452 A | 8/1995 | Hart et al. |
| 5,453,095 A * | 9/1995 | Davila et al. ........... 604/167.04 |
| 5,456,284 A * | 10/1995 | Ryan et al. .................. 137/522 |
| 5,460,616 A | 10/1995 | Weinstein et al. |
| 5,476,475 A | 12/1995 | Gadberry |
| 5,496,280 A * | 3/1996 | Vandenbroek et al. . 604/167.03 |
| 5,534,009 A | 7/1996 | Lander |
| 5,540,661 A * | 7/1996 | Tomisaka et al. ........... 604/265 |
| 5,545,142 A | 8/1996 | Stephens et al. |
| 5,562,632 A | 10/1996 | Davila et al. |
| 5,569,205 A | 10/1996 | Hart et al. |
| 5,578,016 A | 11/1996 | Zinger |
| 5,584,850 A | 12/1996 | Hart et al. |
| 5,599,347 A | 2/1997 | Hart et al. |
| 5,603,702 A | 2/1997 | Smith et al. |
| 5,607,397 A | 3/1997 | Stephens et al. |
| 5,613,954 A | 3/1997 | Nelson et al. |
| 5,618,297 A | 4/1997 | Hart et al. |
| 5,628,732 A | 5/1997 | Antoon, Jr. et al. |
| 5,634,908 A | 6/1997 | Loomas |
| 5,651,771 A | 7/1997 | Tangherlini et al. |
| 5,657,963 A | 8/1997 | Hinchlffe et al. |
| 5,662,215 A | 9/1997 | Focke et al. |
| 5,709,664 A | 1/1998 | Vandenbroek et al. |
| 5,720,730 A | 2/1998 | Blake, III |
| 5,738,664 A | 4/1998 | Erskine et al. |
| 5,782,812 A | 7/1998 | Hart et al. |
| 5,782,817 A | 7/1998 | Franzel et al. |
| 5,788,676 A | 8/1998 | Yoon |
| 5,792,113 A | 8/1998 | Kramer et al. |
| 5,803,919 A | 9/1998 | Hart et al. |
| 5,807,338 A | 9/1998 | Smith et al. |
| 5,813,597 A | 9/1998 | Wakevainen |
| 5,814,026 A | 9/1998 | Yoon |
| 5,820,600 A | 10/1998 | Carlson et al. |
| 5,827,228 A | 10/1998 | Rowe |
| 5,843,031 A | 12/1998 | Hermann et al. |
| 5,882,345 A | 3/1999 | Yoon |
| 5,913,847 A | 6/1999 | Yoon |
| 5,916,198 A | 6/1999 | Dillow |
| 5,916,232 A | 6/1999 | Hart |
| 5,935,107 A | 8/1999 | Taylor et al. |
| 5,984,919 A | 11/1999 | Hilal et al. |
| 5,989,232 A | 11/1999 | Yoon |
| 5,989,233 A | 11/1999 | Yoon |
| 6,010,494 A | 1/2000 | Schafer et al. |
| RE36,702 E | 5/2000 | Green et al. |
| 6,071,265 A | 6/2000 | Bestetti et al. |
| 6,123,689 A | 9/2000 | To et al. |
| 6,159,182 A | 12/2000 | Davis et al. |
| 6,258,065 B1 | 7/2001 | Dennis et al. |
| 6,276,661 B1 * | 8/2001 | Laird ....................... 251/61.1 |
| 6,319,266 B1 | 11/2001 | Stellon et al. |
| 6,402,723 B1 * | 6/2002 | Lampropoulos et al. .... 604/256 |
| 6,416,499 B1 * | 7/2002 | Paul, Jr. ..................... 604/256 |
| 6,482,181 B1 * | 11/2002 | Racenet et al. ........ 604/167.06 |
| 6,551,283 B1 * | 4/2003 | Guo et al. ............. 604/167.06 |
| 6,699,221 B1 * | 3/2004 | Vaillancourt ........... 604/167.01 |
| 2002/0007152 A1 | 1/2002 | Hermann et al. |
| 2002/0013552 A1 | 1/2002 | Dennis |
| 2002/0026207 A1 | 2/2002 | Stellon et al. |
| 2002/0156432 A1 | 10/2002 | Racenet et al. |

* cited by examiner ered. In addition, the present invention will in the preferred embodiments also have an ability to an ability to accommodate medical instruments having various outer diameters within a certain range.

FLOATING SEAL ASSEMBLY FOR A TROCAR

BACKGROUND OF THE INVENTION

The present application is based on and a claim of priority is made pursuant to 35 U.S.C. Section 119(e) to a prior filed, provisional patent application with a filing date of Apr. 26, 2002 and having Ser. No. 60/376,033.

FIELD OF THE INVENTION

This invention relates to a seal assembly of the type normally used with a trocar or like device structured to introduce medical instruments into the body cavity of a patient for purposes of performing surgery. The seal assembly includes a seal member freely movable within a chamber of a seal housing, whether formed as part of the trocar or attached thereto, and generally overcomes recognized disadvantages associated with conventional seal assemblies. By way of example only, the present invention has an ability to better maintain a seal about a medical instrument's outer diameter while the instrument is being manipulated and moved about during a surgery, and is more resistant to being damaged when a medical instrument is being introduced into and/or removed from the trocar. In addition, the present invention will in the preferred embodiments also have an ability to an ability to accommodate medical instruments having various outer diameters within a certain range.

DESCRIPTION OF THE RELATED ART

Laparoscopic surgery has become quite common in recent years as it generally avoids several significant drawbacks associated with previous surgical methods. Those methods involved the making of large incisions into a patient's body so as to give the surgeon clear and unobstructed visual access to the targeted organ(s) or anatomical tissue of the patient for the surgical procedure involved. In stark contrast, the currently favored surgical technique of laparoscopy involves the forming one or more small entry sites in the patient's abdominal wall for accessing his or her body cavity, using a trocar or like device to provide a working channel, and performing surgery on the targeted organ(s) or tissue via a medical instrument inserted into the trocar or like device. Following this type of surgery, patients usually experience significantly less pain and recover much more quickly than when the older surgical methods were used, and as a result, the minimally invasive procedures of laparoscopy have become well accepted in the medical field.

The trocar used in performing laparoscopic surgery typically includes an elongated tube or cannula, and the formation of the small surgical entry site(s) usually involves the insertion of an obturator with a sharp distal tip within the trocar and then pushing through the abdominal tissues until the wall or thick lining of the abdominal cavity is punctured. At that point, the obturator is usually removed from the trocar cannula and the patient's abdominal cavity is inflated with a suitable gas, such as carbon dioxide, to provide space within the abdomen for the surgery to take place. The trocar or like device remains in place at the entry site(s) and functions as a working channel across the abdominal tissues and thick lining of the abdominal cavity, and into that cavity, such that relatively thin and long handled instruments, including forceps, scissors, retractors, dissectors, etc., as well as a tiny video camera and light source, which are all specifically designed for this purpose, may be inserted through the trocar, although there will often be more than one trocar in place during surgery. While positioned in a trocar, the chosen medical instruments are manipulated by the surgeon into contact with the patient's organ(s) or anatomical tissue involved in the procedure.

As noted above, during laparoscopy the patient's abdominal cavity is typically insufflated, usually by the attachment of a source of gas to the trocar assembly, which gas is forced under pressure into the accessed abdominal cavity. Once that cavity is inflated, it is important that the fluid pressure within the body cavity be maintained in order to provide the needed access to the internal organs, as well as adequate room for visual observation during the surgical procedure. Therefore, it is important to prevent the escape of pressurized fluid from within the body cavity, back through the cannula and/or housing associated with the trocar. This is commonly achieved by the use of valves or sealing mechanisms within the trocar, and both "septum" valves and "zero closure" valves are used for this purpose. For example, it is known to use "septum" valves located at the proximal end of the trocar, usually within the trocar's housing, to form a seal around the outer surface of a medical instrument which has been inserted within the trocar. However, these types of seals will not usually prevent the escaping of gas once a medical instrument has been removed from the trocar. As such, it is also known to provide trocars with a "zero closure" valve to prevent gas from escaping when there is no medical instrument present within the trocar.

The present invention relates generally to the type of seal achieved by "septum" valves for sealing about the outer surface of medical instruments. However, there are a number of competing factors to consider in providing this type of seal mechanism, and substantial room for improvements over those which are currently known in the art, as will now be explained.

First, and as indicated above, laparoscopic surgery can involve a variety of medical instruments during any given surgical procedure and there are also a number of manufacturers of such instruments. Accordingly, among other things, the outer diameters of these medical instruments can and do vary. For example, it is quite common for the outer diameters of such medical instruments to vary within a conventionally current range from about 3 mm to 15 mm. This fact, however, presents an obstacle for preventing the escape of gas by or via the septum valve because the valves known or used for this purpose typically accommodate and effectively seal against only one set size of a medical instrument's outer diameter or one sized very closely thereto.

This, in turn, causes some disruption in the performance of the surgery. For example, the septum valve seal will not perform adequately when a medical instrument having a smaller outer diameter than the set size offered by the septum valve must be used, meaning that some gas will escape, the abdominal cavity may have to inflated again, etc. As another example, if a medical instrument having a much larger outer diameter must be used, which is beyond the size of the septum valve, there may be an unacceptable drag or friction force exerted on the instrument during its insertion into or removal from the trocar, and while its is being manipulated during surgery. Further, the septum valve may become ripped, torn or otherwise damaged, leading to a loss of insufflation gas and/or a need to replace the trocar, etc. during surgery.

Some in the art have attempted to solve this problem by providing an attachment device for the trocar, which provides another or supplemental septum valve to accommodate the use of medical instruments having differently sized outer diameters during surgery. However, such devices must still be manipulated and/or somehow attached to the trocar to permit use during surgery, which interrupts the surgery somewhat and which can be cumbersome if the user's hands are wet, bloodied, slippery, etc.

Second, and as also noted above, during laparoscopic surgery the trocar remains inserted across the patient's abdominal tissues, wall, and into the abdominal cavity, acting as the working channel into which the various medical instruments are inserted or removed. However, during a surgery the trocars are often disposed at various angles, meaning that when a medical instrument is introduced into the trocar, and even during the surgery itself, it will often be oriented in an angularly, off-set position relative to the trocar, meaning the instrument is out of axial alignment with the central axis of the trocar housing, including with any septum valve associated therewith. This, in turn, also causes some disruption in the performance of the surgery. For example, known septum valves are usually made of a very thin, flexible material which can be punctured or ripped when a medical instrument is inserted at an angle, which can result in the loss of some insufflation gas during surgery, delay if the trocar must be replaced, etc. Also, while a surgery is in progress the manipulation of medical instruments within the trocar has been known to cause the septum valves to become "egg-shaped," which typically results in the loss of some insufflation gas.

Despite the recognition of these and other obstacles, and attempts to address them, there remains an appreciable need for an improved mechanism or assembly for sealing about the outer surface of medical instruments used in trocars or like devices. Any such improved sealing mechanism should be suitable for and readily used with a trocar assembly or like device, and further, should effectively maintain insufflation pressure within a patient's body cavity, once it has been accessed and inflated. Any such improved sealing mechanism should also accommodate and/or facilitate the introduction of medical instruments into the trocar, even when oriented in an angular, off-center position relative to the longitudinal axis of the trocar and/or the inlet port associated therewith, and should also resist the formation of ovals or "egg-shapes," especially when the medical instrument is being forcably manipulated and otherwise used during surgery. Further, any such improved sealing mechanism should be structured to prevent or significantly reduce the possibility of damage thereto, especially when the seal assembly comes into contact with the distal end of a medical instrument being introduced. Any such improved sealing mechanism would preferably also be capable of accommodating a number of medical instruments, including ones having various outer diameters, such as, but not limited to, those falling within the currently conventional range of about 3 mm to 15 mm. Ideally, any such improved sealing mechanism would also accomplish all of the foregoing without creating excessive drag or friction on the medical instrument while it is being inserted into or removed from a trocar or otherwise moved about during the performance of the surgery.

SUMMARY OF THE INVENTION

The present invention presents a solution to these and other needs which remain in this field of art and is directed to a seal assembly that is primarily structured to be used with a trocar or like device that facilitates the introduction of medical instruments through an anatomical wall and into the interior of a body cavity of a patient, such as during laparoscopic surgery. The seal assembly of the present invention incorporates an inventive seal member, features of which are discussed in detail subsequently herein, and as such, the present application includes some claims drawn to the seal member, alone, as well as to the inventive seal assembly.

More specifically, the seal assembly of the present invention includes a seal member that is structured to be freely movable or "floating" within the interior of a chamber, which may be formed within the housing of a trocar or formed separately and attached to the trocar. The seal assembly is structured to allow for and accommodate the passage of a plurality of medical instruments there-through, and preferably, instruments having differently sized, outer diameters. As noted previously herein, medical instruments used in laparoscopic surgery are currently available with outer diameters that fall into a conventional range of about 3 mm to 15 mm, and while the present invention can, in one embodiment, accommodate a narrower range of instruments' outer diameters, such as 5 mm to 8 mm and/or in another embodiment about 10 mm to 12 mm, it will ideally be able to seal about a wider range of instruments' outer diameters, such as but not limited to the conventional range noted above.

The seal member of the present invention is formed of an elastomeric material, and is preferably of an integral, one piece construction. The seal member includes oppositely disposed, first and second outer surfaces and a channel extending there-through in communicating relation with the first and second outer surfaces. The channel is preferably, but not necessarily, centrally disposed within the seal member. The seal member includes at least one interior surface, if not two interior surfaces, which at least partially define both the configuration and the boundaries of the channel. The interior surface or surfaces associated with the channel is/are disposed and structured to movably engage the exterior surface of any medical instrument passing through the channel, and further, is/are sized, configured and otherwise structured to maintain sealing engagement about the exterior of the instrument, despite the fact that the outer diameter of the instruments may vary, as noted above.

Also, at least the first outer surface of the seal member is configured to accommodate the introduction of a medical instrument in an angled or skewed orientation to the channel. More in particular, during a laparoscopic surgical procedure it is quite common for medical instruments to be introduced into the trocar in an orientation which is not perfectly aligned with the central longitudinal axis of the trocar housing or cannula. This angled or skewed orientation of the instrument as it is being introduced into the trocar has been known to cause damage to previously known sealing mechanisms within the trocar, due to the exertion of substantially obliquely directed forces, and especially in situations where the distal end of the instrument carries scissor blades, clippers or is otherwise sharp. However, the seal assembly of the present invention overcomes such disadvantages by providing a seal member which freely moves or "floats" within a chamber. Therefore, upon introduction of a medical instrument, the seal member is capable of moving laterally within the chamber to accommodate the introduction of the instrument in an angled or skewed orientation, i.e., one which is not in alignment with the intended direction of travel of the instrument down the central axis of the trocar cannula. In addition, and as noted above, the seal member has in a preferred embodiment at least its first outer surface of the seal member, if not the oppositely disposed, second outer surface as well, configured to facilitate the passage of the distal working tip of the medical instrument into the interior of the channel and along the interior surfaces thereof. For example, the illustrated embodiment depicts an interior surface at the open end of the channel as having a flared configuration.

The seal assembly of the present invention also comprises a cooperative dimensioning between the seal member and the interior of the chamber in which the seal member is floatingly or movably disposed. More specifically, the height dimension of the seal member is sized to maintain sealing engagement between the first and second outer surfaces of the seal member with correspondingly positioned inner surfaces of the chamber, as may be defined, for example, by an upper wall or ceiling corresponding a seal cap and a lower wall or floor corresponding a seal body or portion of the trocar's housing. As described more in detail subsequently herein, while this cooperative dimensioning allows for sealing engagement, it should also be such as to allow the seal member to move relatively freely or float within the chamber. In addition, the diameter of the seal member is also sized to maintain sealing engagement within the chamber, e.g., relative to the inlet port, through which the medical instrument is introduced and relative to the outlet port through which the medical instrument extends into the cannula of the trocar and the patient's body cavity. More specifically, the diameter of the seal member is sized relative to the inner diameter of the chamber such that the seal member is disposed in generally surrounding relation to the inlet port, even though it may not be completely concentric therewith. Accordingly, the introduction of a medical instrument into the seal assembly will be facilitated, and in addition, when a medical instrument is disposed within the seal assembly, a fluid tight seal will be maintained between the seal member and the upper inner surface or ceiling of the chamber surrounding the inlet port, regardless of the position of the seal member within the chamber.

As noted above, the seal assembly of the present invention includes a seal member that is capable of moving freely in at least a lateral or radial direction within the seal chamber, and yet, sealing engagement is still provided by the seal member about the exterior surface of a medical instrument inserted into the channel thereof. In addition, sealing engagement is provided for within the chamber itself, around the peripheral surfaces of the seal member and between the lower and upper interior surfaces of the chamber, due to the cooperative dimensioning between the seal member and the interior of the chamber, as noted above. As such, the present invention readily accommodates the frequent manipulation of the medical instrument introduced into the body cavity by the surgeon in a number of directions without allowing a leak to form or the insufflated gas to otherwise escape.

These and other objects, features and advantages of the present invention will become more clear when, the drawings as well as the following detailed description of the invention in one or more preferred embodiments, are taken into consideration.

BRIEF DESCRIPTION OF THE DRAWINGS

For a fuller understanding of the nature of the present invention, reference should be had to the following detailed description taken in connection with the accompanying drawings in which:

FIG. 4-B is a perspective view of the seal assembly illustrated in FIG. 4-A assembled and attached to the trocar assembly illustrated in FIG. 1.

Like reference numerals refer to like parts throughout the several views of the drawings.

DETAILED DESCRIPTION OF THE INVENTION IN PREFERRED EMBODIMENT(S)

Figure 1:
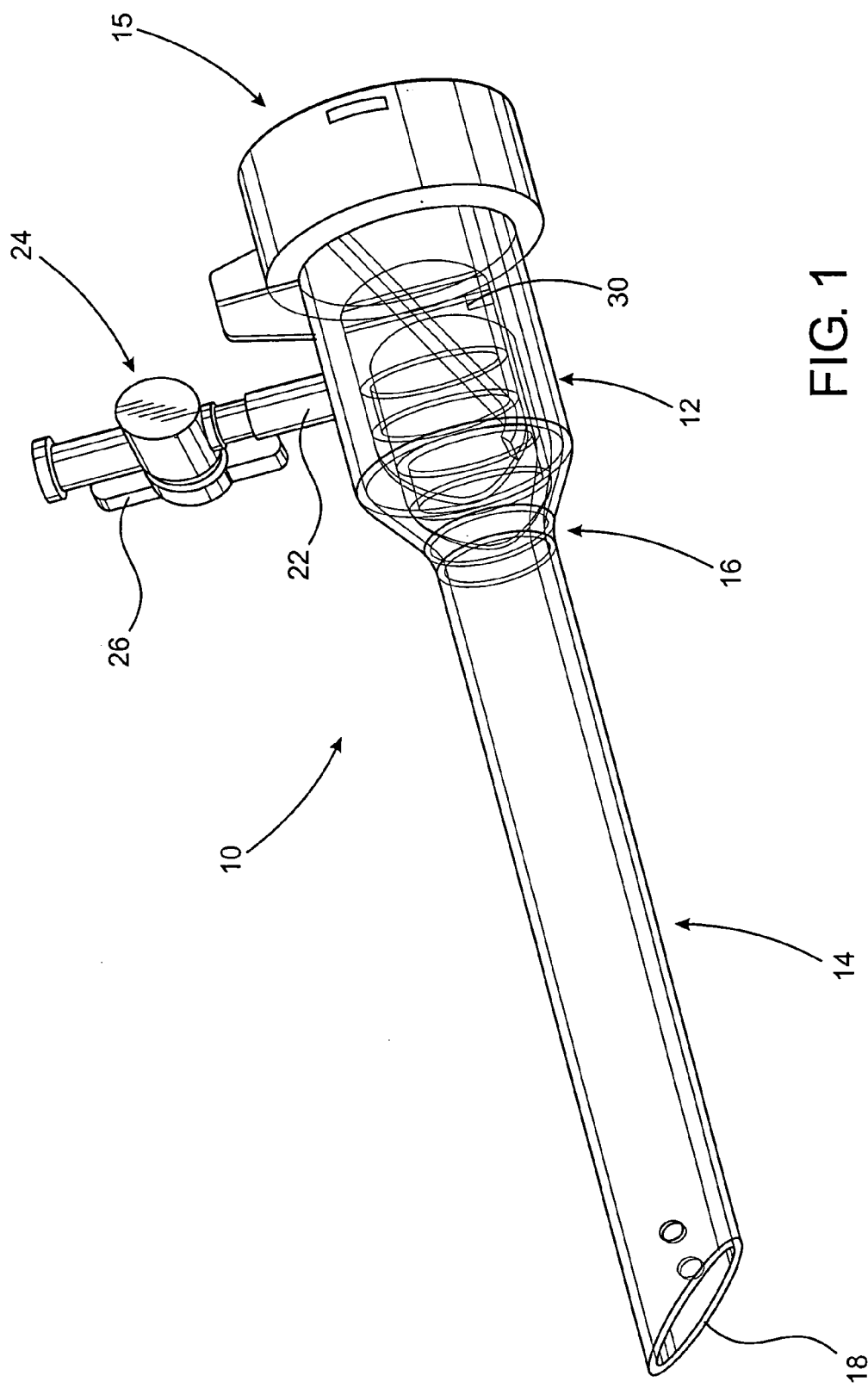
FIG. 1 is a perspective view of one possible type of a trocar assembly with which the seal assembly of the present invention may be utilized.

The present invention is directed to a seal assembly that is primarily structured to be used with a trocar 10, as shown in FIG. 1, or a like device associated with the introduction of medical instruments through anatomical tissues and into the body cavity of a patient, such as during laparoscopic surgery. It is to be understood at the outset that the present invention is susceptible of embodiment in different forms. While there is shown in the drawings and will be described in detail herein at least one specific embodiment, it is with the understanding that the present disclosure is to be considered as an exemplification of the principles of the invention which should not limit the invention to the embodiment or embodiments illustrated.

With initial reference to FIG. 1, there is illustrated one possible type of a trocar assembly, indicated generally as 10, with which the seal assembly of the present invention may be used. The present invention is, however, readily suitable for use with other types of trocars. Generally, the trocar assembly 10 includes a housing 12 and an elongated hollow sleeve or cannula generally indicated as 14 either attached to or integral with a distal end of the housing 12, as at 16. The opposite end 18 of cannula 14 is open to allow the distal working end of medical instruments inserted into the trocar 10 to pass into the patient's body cavity for use during surgery, and also to allow insufflation fluid to pass into the body cavity. In particular, the trocar housing 12 will typically include a port or coupling, such as that illustrated at reference numeral 22, which is disposed and configured to receive a connector generally indicated as 24. The connector 24 is structured for attachment to a source of gas or insufflation fluid which is to be introduced into the port or coupling 22 under pressure. The insufflation fluid may be carbon dioxide or another commonly use gas conventionally employed to inflate and expand the internal body cavity of a patient and thereby, permit a surgical procedure to be performed by providing increased working space within the body cavity. The connector 24 may include a control knob 26 which regulates fluid flow of the gas into the interior of the trocar housing 12 through the connector 24.

As explained previously herein, the trocar assembly 10 is structured to receive any one of a variety of medical instruments. For example, one type of medical instrument might be an elongated rod having a pair of small scissors formed at its distal working end and a small handle at its proximal end. The distal working end of the medical instrument is initially introduced into the trocar housing 12 at proximal end 15 and passed through the trocar housing 12 and along the length of the cannula 14. As has also been described, and as is generally known in the art, the medical instrument is of a length sufficient to permit its distal working end to extend beyond the open end 18 of the trocar cannula 14 and carry out surgery on the targeted organs of the patient, by the surgeon's manipulation of the handles attached to the instrument, which remain disposed outside the trocar housing's proximal end 15 during surgery. The housing 12 and cannula 14 of the trocar include an at least partially hollow interior disposed in communicating relation with each other in order to that the medical instrument may pass there-through. It will be noted from FIG. 1 that both the housing 12 and cannula or sleeve 16 of the trocar 10 are represented as being transparent. However, this is primarily for illustration purposes only, as the housing 12 and cannula 16, as well as other portions of the trocar assembly 10, are typically formed of an opaque and/or translucent material.

As described previously herein, during surgery it is important to prevent the escape of pressurized gas from the patient's body cavity, and as such, the trocar assembly 10 includes one or more valve or sealing mechanisms to accomplish this. For example, the trocar housing 12 will often include a "zero closure" valve, such as but not limited to a flapper and/or "duck bill" type of valve, which can be opened to allow passage of the medical instrument but which prevents gas from escaping once the instrument has been removed from the trocar 10. Illustrated in the trocar housing 12 of FIG. 1, however, is an inventive and proprietary valve assembly 30 which has been disclosed in a currently pending U.S. patent application, namely, Ser. No. 09/870,112, filed on May 30, 2001, incorporated herein in its entirety by reference. Also, most trocars include another valve or sealing mechanism to form a seal around the outer surface of a medical instrument when one is present within the trocar, and a "septum valve" is often utilized for this purpose. With reference to FIG. 1, a septum valve can be incorporated into the trocar assembly 10 at its proximal end 15. The present invention, however, provides an improvement in this latter type of seal, i.e., for sealing about the outer surface of medical instruments.

Figure 2:
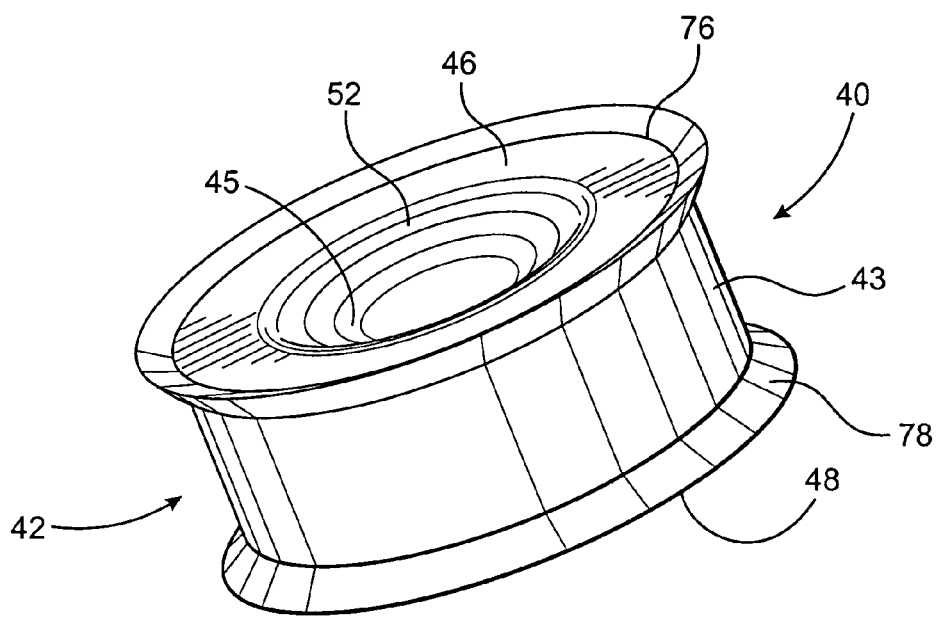
FIG. 2 is a perspective view of the seal member of the present invention in a preferred embodiment.
Figure 3:
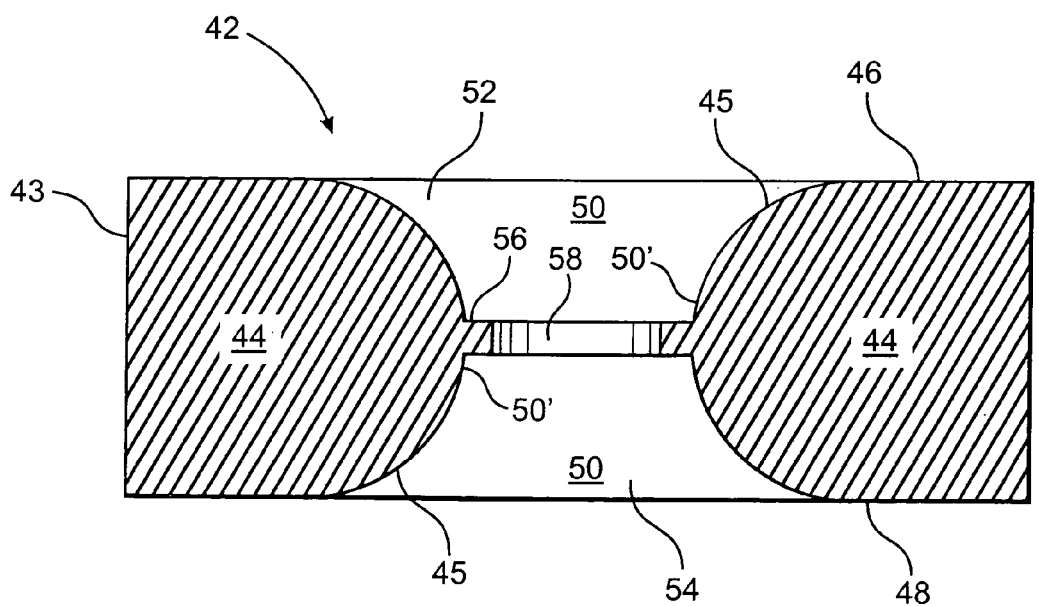
FIG. 3 is a schematic cross-sectional view of the seal member of the present invention in another embodiment.

The present invention is directed to a seal assembly 40, one embodiment of which is illustrated in FIGS. 2 through 4. It is currently intended by the inventor hereof that the seal assembly 40 functions in cooperation with another valve assembly mounted at least partially within the trocar housing 12, such as that indicated in FIG. 1 by reference numeral 30, for preventing a sealing mechanism when there is no medical instrument passing within the trocar. It is possible, however, that the seal assembly 40 of this invention could be used without a valve assembly 30, but also, that it could be used with a variety of other valve structures, aside from the valve assembly 30 illustrated in FIG. 1.

Figure 4A:
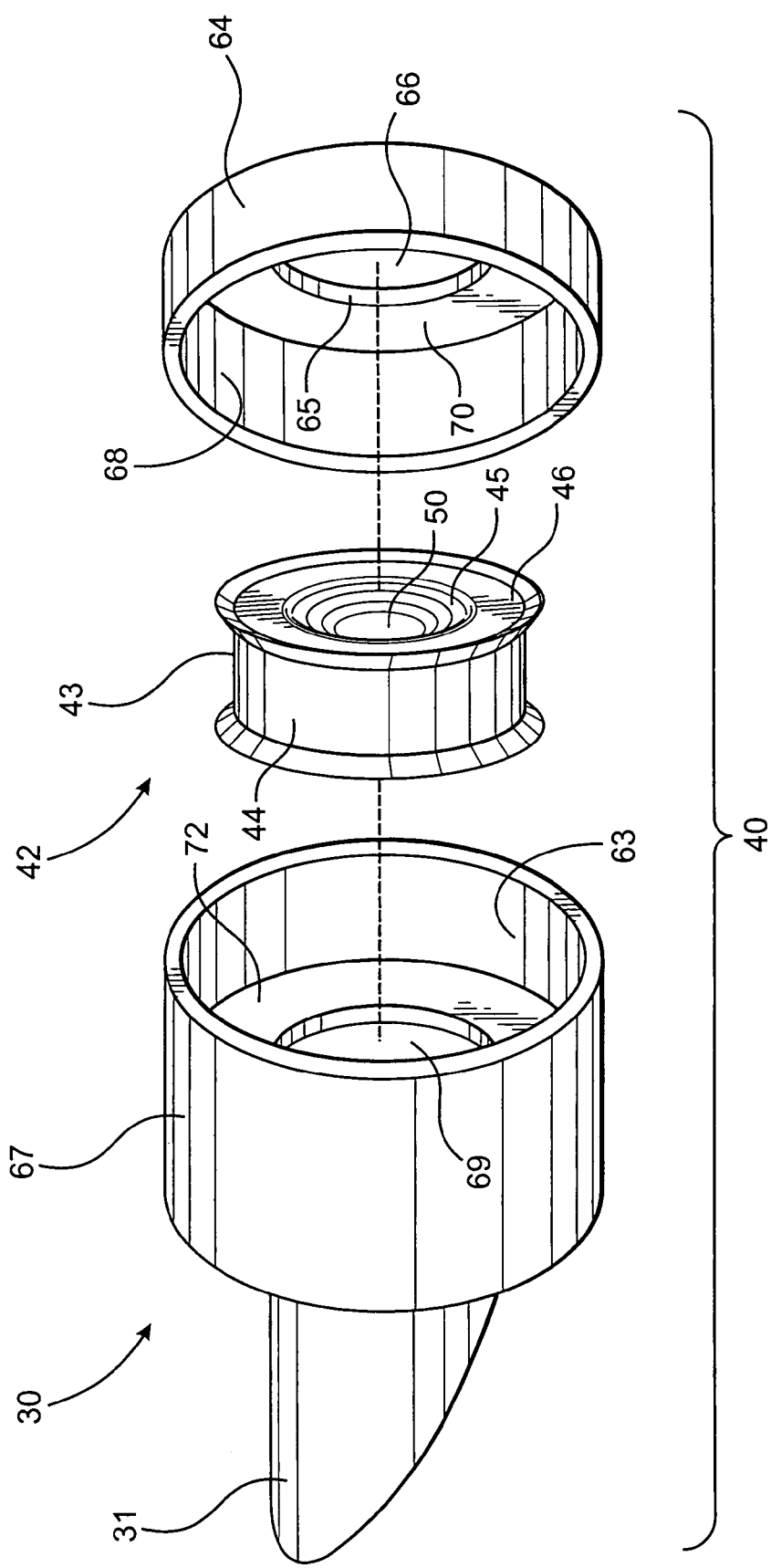
FIG. 4-A is a perspective view in exploded form of a seal assembly according to the present invention, including a seal housing and seal closure or cap, in which a seal member such as that shown in FIG. 3 is operatively disposed.
Figure 4B:
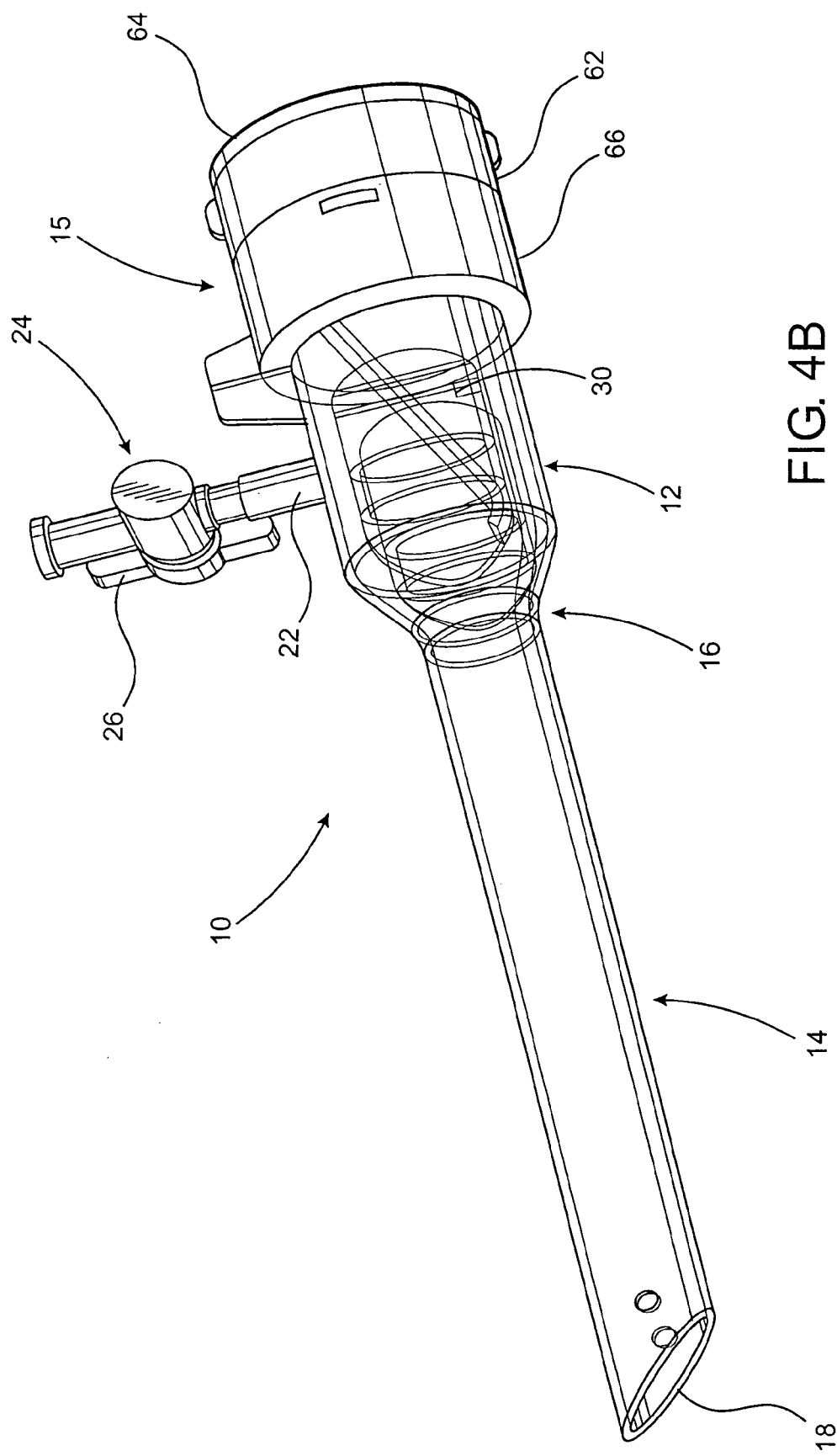
Figure 5:
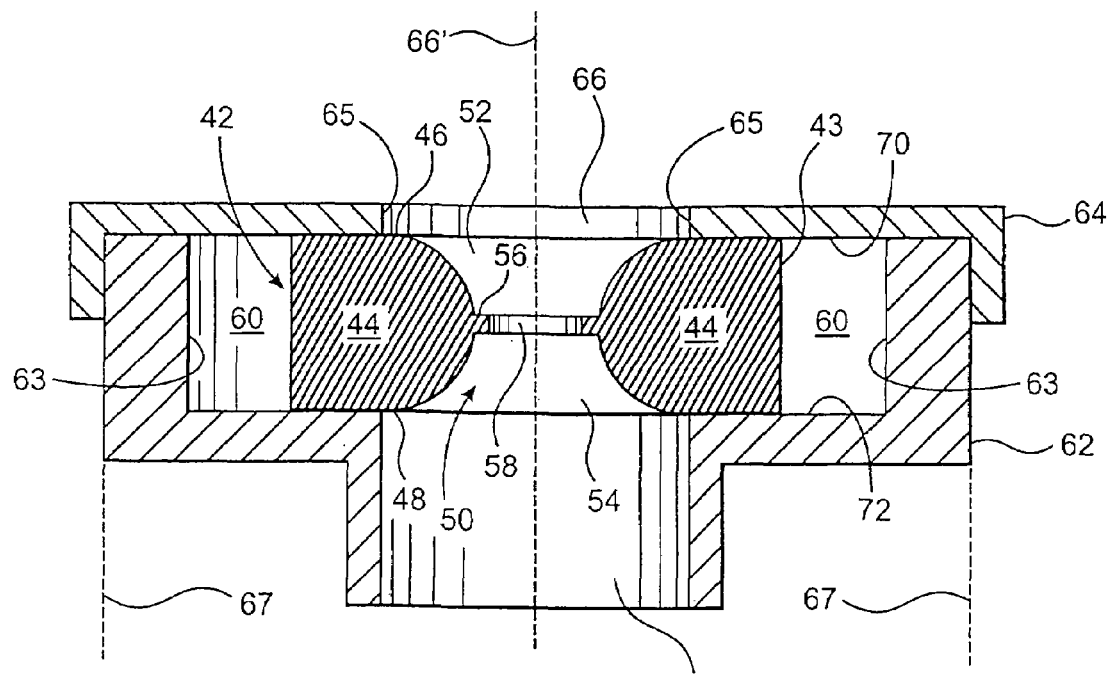
FIG. 5 is a schematic cross-sectional view of the seal assembly of the present invention shown in an assembled, operative position and more clearly illustrating the seal member disposed and/or sandwiched within a chamber, formed in this embodiment by the seal closure or cap partially receiving the seal housing.

As illustrated in FIGS. 3 through 5, the seal assembly of the present invention is shown in one embodiment and is indicated generally as 40. The seal assembly 40 comprises a seal member 42 formed of an elastomeric material and which preferably, but not strictly necessarily, comprises an integral, one piece construction. The elastomeric material used to form the seal member 42 can be silicone or polyurethane or other material, such as a urethane compound, rubber-like compound, etc. The seal member 42 can be formed by suitable means such as injection molding or the like, and while it may be formed to have a hardness in the range of fifty (50) durometers, it can be less, and potentially significantly less such as in the range of three (3) durometers, so as to more readily accommodate a wider range of medical instruments' outer diameters and provide less frictional forces on a medical instrument as it is moved into and of the trocar 10.

As is perhaps best illustrated in FIGS. 2, 3 and 4A, the seal member 42 is defined by a body 44 having a first outer surface 46 and a second, oppositely disposed outer surface 48 and a generally cylindrical body wall 43. Moreover, the body 44 of seal member 42 includes a channel or bore 50 extending completely there-through, with oppositely disposed open ends 52 and 54. As best shown in FIG. 3, the open ends 52 and 54 are disposed substantially contiguous to the first and second outer surfaces 46 and 48, respectively. Also, the body of seal member 42 has an interior surface 45 which is disposed in surrounding relation to the channel 50, including at least one of the opposite open ends, such as 52, such that the interior surface 45 substantially defines the boundaries of the channel 50. At least one of the open ends of the channel 50, such as end 52 defined by interior surface 45, includes, although both open ends 52 and 54 can and preferably will include, a substantially flared configuration such that they diverge outwardly from a mid-portion or interior of the channel 50, indicated by 50' in FIG. 3, towards the respective outer surfaces 46 and 48 of the seal member 42.

As has been described, the seal assembly 40 is structured and primarily intended for use with a trocar assembly 10, such as but not limited to the type disclosed in FIG. 1. Referring now to FIGS. 4A–4B and FIG. 5, it will be seen that once assembled and in an operative position, the seal assembly 40 includes the seal member 42 being captured but freely movable within a chamber 60 formed within a seal housing 62. For example, the housing of the trocar 12 can be formed to include at its proximal end 15 a floor or lower portion 72 of the chamber 60, and a closure or seal cap 64 can be fixedly or removably connected to the seal housing 62 to define the chamber 60 within the seal housing 62, as best shown in these Figures. In FIGS. 4-A and 4-B, the seal housing 62 is illustrated as being disposed in communicating relation with a valve housing 67 that is part of and/or that is movably disposed within the housing 12 of the trocar 10. The valve housing 67 is part of a valve assembly 30, described previously, that is considered an inventive and/or proprietary embodiment for which separate patent protection is currently pending, although it is pointed out that other valve assemblies 30 can be utilized with the seal assembly 40 of the present invention.

As also shown in FIGS. 4A–5, the closure or seal cap 64 includes an inlet port 66 directly communicating with the chamber 60 and the seal member 42 movably disposed therein. The inlet port 66 is dimensioned to accommodate the passage therethrough of a variety of medical instruments, each of which may have a differently sized outer diameter falling within the conventional range of about 3 mm to 15 mm. Because the seal cap 64 is made of a rigid material, such as plastic, the port 66 can be sized for example to receive instruments having the largest outer diameter, such as 12 mm or 15 mm. Alternatively, the inlet port 66 of seal cap 64 can be sized to receive smaller outer diameter instruments, but accommodating those having the largest outer diameter relative to a specified range, such as 5 mm–8 mm for instance. Regardless, the closure or seal cap 64 is preferably fixedly secured to form the seal housing 62, such as by bonding, etc. or alternatively, it could be structured to be removably connected and/or snapped on to form the seal housing 62. As another alternative, the seal housing 62 could be formed and/or assembled into one integral piece including the seal member 42 therein, for attachment onto the proximal end 15 of a trocar, as illustrated generally in FIG. 1.

As shown in FIG. 4-A, a medical instrument introduced into the trocar assembly 10 illustrated in FIG. 4-B, will initially pass through the inlet port 66 and seal cap 64 and then through channel 50 of the seal member 42, wherein at least a mid-portion or interior 45 of the channel 50 establishes sealing engagement with the exterior thereof. Continued travel of the instrument causes it to pass through valve housing 67 and aperture 69 thereof, and through a valve mechanism such as seat 31 or other components of a valve assembly 30, located "downstream" of the inlet port 66 and seal member 42. With the medical instrument inserted into the trocar 10, the valve assembly 30 is or will be disposed in an open position and as such the instrument is permitted to continue travel through the trocar 10 and cannula 14 to establish communication with the interior of the patient's body cavity being accessed. While it then becomes possible for insufflation gas forced into the patient's body cavity to travel "upstream" into the trocar cannula 14 and housing 12 and beyond the valve assembly 30, since it is maintained in an open position, the seal assembly 40 is disposed, dimensioned, configured and structured to prevent escape of the insufflation gas beyond the seal housing 62, as will be explained more specifically hereinafter.

Referring now to FIG. 5, the seal member 42 is shown in an operative position within the chamber 60 of seal housing 62 and as described, while captured within the chamber, is still relatively free to move within the chamber 60. As illustrated, the first and second outer surfaces 46 and 48 of the seal member 42 are respectively disposed in sealing engagement with correspondingly positioned inner surfaces of the chamber 60. Specifically, the first outer surface 46 of the seal member body 44 is disposed in movable, sealing engagement with the inner surface 70 of the closure or seal cap 64. Similarly, the second outer surface 48 of the seal member body 44 is disposed in movable sealing engagement with the inner surface 72 of the valve housing 67 or other structure creating a floor for the seal housing 60. Further, the seal member 42 and the chamber 60 are cooperatively dimensioned such that regardless of the position of the seal member 42 within the chamber 60, the height dimension of the seal member body 44 and/or its body wall 43 is sufficient to at least maintain a peripheral portion of the first and second outer surfaces 46 and 48 in sealing contact with the respective inner surfaces 70 and 72. In addition, the seal member 42 and the chamber 60 are cooperatively dimensioned such that the outer diameter of the seal member 42 relative to the inner diameter of the chamber 60 is such as to maintain the seal member 42 in generally surrounding relation relative to at least the inlet port 66, and also preferably to the outlet port 69 of the valve housing 67, and thereby, prevent gas from escaping out the inlet port 66 of closure or seal cap 64.

As clearly disclosed in FIGS. 4A and 5, however, the seal member 42 of the seal assembly 40 is unattached or unconnected to the seal housing 62, seal closure 64 or any other associated portion of the trocar housing 12. As such, the seal member 42 is freely movable, at least in a lateral or radial direction within the chamber 60, until such movement is limited by a contact between the outer cylindrical body wall 43 of the seal member 42 with the inner wall surface 63 or 68 of the chamber 60. In use, the seal member 42 can frequently be and will often be out of an axial alignment with a central longitudinal axis of the inlet port 66 and/or of the chamber 60, as schematically represented in FIG. 5 by phantom line 66'. This is true regardless of whether a medical instrument is being inserted into or has already been inserted into the seal assembly 40 and trocar assembly 10. This is also true when the instrument has been removed therefrom altogether as there is no biasing structure or other structure contemplated for causing the seal member 42 to be in or return to concentric alignment with the longitudinal axis 66' and/or with the port 66. However, the amount of displacement of the seal member 42 out of axial alignment with the central longitudinal axis 66' of the inlet port 66 is limited, as described above, by the cooperative dimensioning of the diameter of the outer body wall 43 of the seal member 42 relative to the inner diameter of the chamber 60, such that the seal member 42 is disposed in generally surrounding relation to the inlet port. For instance, the cooperative dimensioning of the seal member's outer diameter relative to the inner diameter of the chamber 60 should be capable of preventing the outer body wall 43 of the seal member 42 from moving enough within the chamber 60 so as to appear within the aperture defining port 66, which could interfere with the introduction of an instrument into port 66, and/or more likely, into channel 50 of the seal member 42.

This inventive feature of the seal assembly 40 offers several advantages. As one example, it more readily accommodates the frequent occurrence of a medical instrument being introduced into a trocar assembly 10 in an off-center or non-aligned manner relative to the central longitudinal axis of the trocar, or in this case to central longitudinal axis 66' through the inlet port 66 of seal cap 64, as shown in FIG. 5. That is, it is well known in the medical field that the introduction of a medical instrument frequently occurs with the instrument being in an off-set, somewhat angularly oriented and/or non-aligned orientation relative to the central longitudinal axis of the trocar 10. With the present invention, the working distal tip of the medical instrument being introduced in a non-aligned manner will engage the seal member 42, and more particularly, the interior surface 45 thereof which defines the first open end 52 of the channel 50. As has been described, the flared configuration of interior surface 45 more readily accommodates the non-aligned introduction of a medical instrument. Also, however, the ability of the seal member 42 to freely move or "float" within the chamber 60 will facilitate the lateral displacement of the seal member 42 towards an inner side wall surface 63 of the chamber 60 in response to the instrument being introduced in a non-aligned manner. As a result, the seal member 42, and the channel 50 or aperture 58 within it in particular, is less likely to be damaged, whether punctured or otherwise. As another example, the seal assembly 40 of the present invention also more readily maintains sealing engagement with the exterior surface of the medical instrument while it is being used during a surgery. That is, it is quite common for medical instruments, once passed through the trocar and into a patient's body cavity, to be pushed on and moved out of alignment with the longitudinal axis of the trocar, and this can often cause other sealing structures to form an oval or "egg shape." The present invention, however, which allows the seal member 42 to move relatively freely within the chamber 60, accommodates this non-axial or out of alignment maneuvering of the instrument(s) during a surgery, and prevents the escape of pressurized gas from the seal assembly 40. As set forth above, with the present invention, sealing engagement is still maintained even when the seal member 42 is laterally displaced, such that the outer body wall 43 or a portion thereof moves towards an inner side wall surface of the chamber 60 (such as at 63 or 68 in FIG. 4-A), typically until the shaft or rod of the medical instrument contacts the wall 65 defining the inlet port 66 in the seal cap 64. In addition, the cooperative dimensioning between the seal member 42 and the chamber 60 maintains sealing engagement, at least about the peripheral portions of the first and second outer surfaces 46 and 48, with the correspondingly disposed inner surfaces 70 and 72 of the closure or seal cap 64 and seal housing 62.

In order to facilitate the introduction of a medical instrument into the channel 50 and movement of the instrument within the assembly 40 with less friction, the seal member 42 is preferably structured to have lubricating characteristics, which should also facilitate the free "floating" travel of the seal member 42, at least in a lateral or radial direction, within the chamber 60. Such lubricating characteristics can be provided by coating the seal member 42, and particularly, the first and second outer surfaces 46 and 48 with a lubricant, such as with a coating of the polymer, parylene. Naturally, other lubricant coatings may be used and/or the elastic material of the base 44 can be made from a plastic material of a sufficiently low durometer to be slippery or to otherwise have inherent lubricating characteristics.

Referring now to FIG. 2, there is illustrated a more preferred embodiment of the seal member 42. This embodiment of the seal member 42 includes at least one sealing flange, but preferably, two sealing flanges, such as 76 and 78, as shown. The sealing flange or flanges 76 and 78 may be integrally formed with the seal member 42 continuously about the outer periphery of the respective, first and second outer surfaces 46 and 48. The sealing flange or flanges 76 and 78 preferably include a continuous or annular configuration which is/are further structured to extend laterally outward and beyond the respective outer surfaces 46 and 48. Each flange will also preferably have, for example, a small height dimension compared to the height dimension of the seal member 42, which in one embodiment may be as small as seven-thousandths (0.007), and further in the same embodiment, may angle upwardly at an angle of about ten degrees. The flange or flanges 76 and 78, and their orientation is believed to reliably maintain a movable sealing engagement of the seal member 42 with the respective inner surfaces 70 and 72 of the chamber 60, even when the transverse dimension of the seal member 42 does not precisely correspond to the transverse dimension of the chamber 60. By way of example only, in certain situations where the seal member 42 has at least a minimally less transverse dimension than that of the chamber 60 (e.g., the depth of the chamber 60), the respective sealing flanges 76 and 78, extending outwardly and beyond the corresponding outer surfaces 46 and 48, will maintain sealing engagement with the inner surfaces of the chamber 60, such as at 70 and 72, and although operating under a greater compression force should still move relatively smoothly and freely within the chamber 60. Therefore, regardless of the lateral displacement of the seal member 42 upon introduction of a medical instrument through the inlet port 66, a sealing engagement will be maintained and established at least about the periphery of the outer surfaces 46 and 48, due at least in part to the structure and disposition of the sealing flanges 76 and 78. Further, the sealing flanges 76 and 78 may have a greater elasticity than the majority of the seal member 42 due to their dimensions being small and/or thin. Of course, while the sealing flanges 76 and 78 may be attached or bonded onto the seal member 42, they are preferably integrally formed with and from the same elastomeric material as the seal member 42, including of the same durometer/hardness as well.

As set forth above, the seal member 42 of the seal assembly 40 is structured to accommodate sealing engagement with the exterior surface of a variety of medical instruments introduced through the channel 50, even when the diameter of such instruments vary, such as within the conventional range of about 3 mm to 15 mm or a smaller range thereof. As shown in FIGS. 3 and 5, the seal member 42 may include in one embodiment, but does not have to include, a web structure 56 in order to facilitate sealing engagement between the seal member 42 with the exterior surface of the smaller diameter instruments, such as in the range of 5 mm. The web structure 56 may be integrally formed with or applied to the seal member 42 on the interior of the channel 50 at approximately a mid portion thereof, and extends radially inward in surrounding relation to a centrally disposed aperture 58 extending through the web structure 56. Also, the web structure 56 may have an annular configuration which substantially surrounds the aperture 58. In order to adequately provide sealing engagement with the medical instruments of larger diametrical dimension, the transverse dimension of the channel 50 may in fact be made at least minimally larger than the 5 mm smaller diameter instruments. Accordingly, the provision of the web structure 56 should accommodate instruments having smaller diameters which may be equal to or less than the normal diameter of the channel 50. Therefore, when a smaller diameter instrument (in the range of 3 mm or 5 mm) is introduced through the channel 50, the exterior surface thereof will be sealing engaged, primarily by the annularly configured web structure 56, rather than a majority of the interior surface 45 of the remainder of the channel 50.

Figure 9:
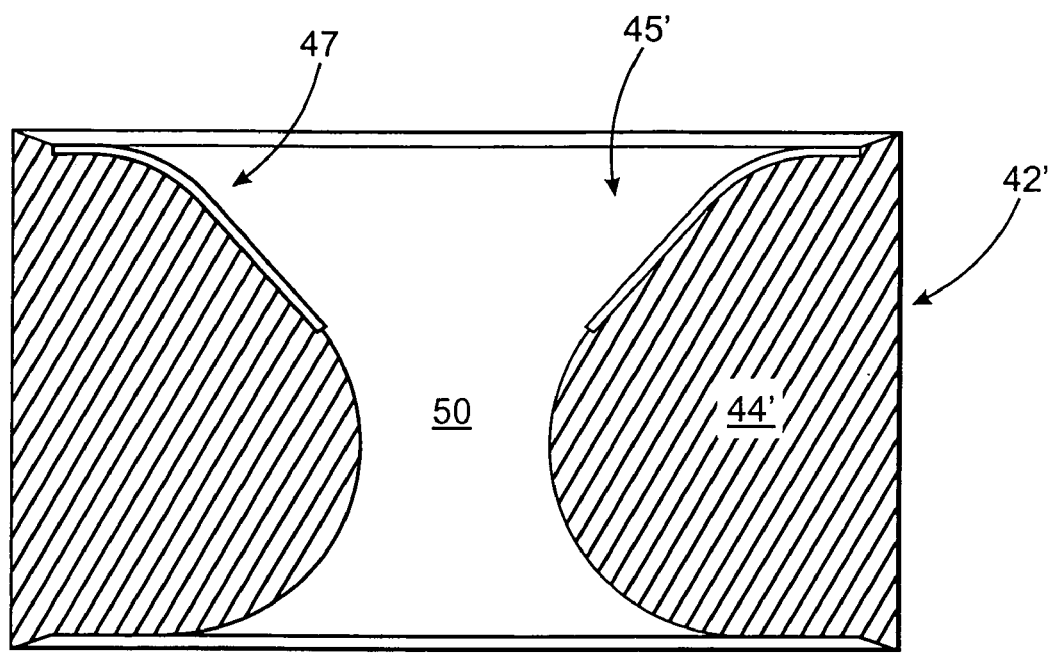
FIG. 9 is a schematic, cross-sectional view of a seal member according to the present invention in yet another embodiment.

With reference now to FIG. 9, the seal member 42' is shown in another embodiment in a cross sectional view. In this embodiment, the seal member 42' is formed to have at least two layers of materials, each with a different hardness or flexibility. For example, the main body 44' of the seal member may be formed to be soft and flexible, such as in the range of zero (0) to five (5) or more, such as (10) durometers. In the illustrated embodiment, the interior surface 45' of the seal member 42' is formed to have a second layer or skin 47 having a harder, less flexible material, such as but not limited to, one in the range of fifty (50) to eighty (80) durometers. By way of example only, this skin 47 or layer may be more flexible, such as thirty (30) durometers, and may have a depth of about 0.010 or ten thousandths in depth. Ideally, this layer of harder skin 47 is disposed entirely or substantially completely about the interior surface 45' of the seal member 42' which defines the open end of the channel 50, and may only need to extend to or towards, if it extends at all, into the interior portions of the channel 50 towards an approximate mid-portion thereof. It is contemplated by the inventor hereof that this skin 47 with more firmness will resist damage, such as being punctured etc., upon the insertion of a medical instrument in an off-center or non-aligned manner. The seal member of this embodiment may be formed in various ways, such as by a two-step silicone molding process using core pin and one or two molds, or by separately bonding or otherwise attaching the layers of different material hardness together.

Figure 6:
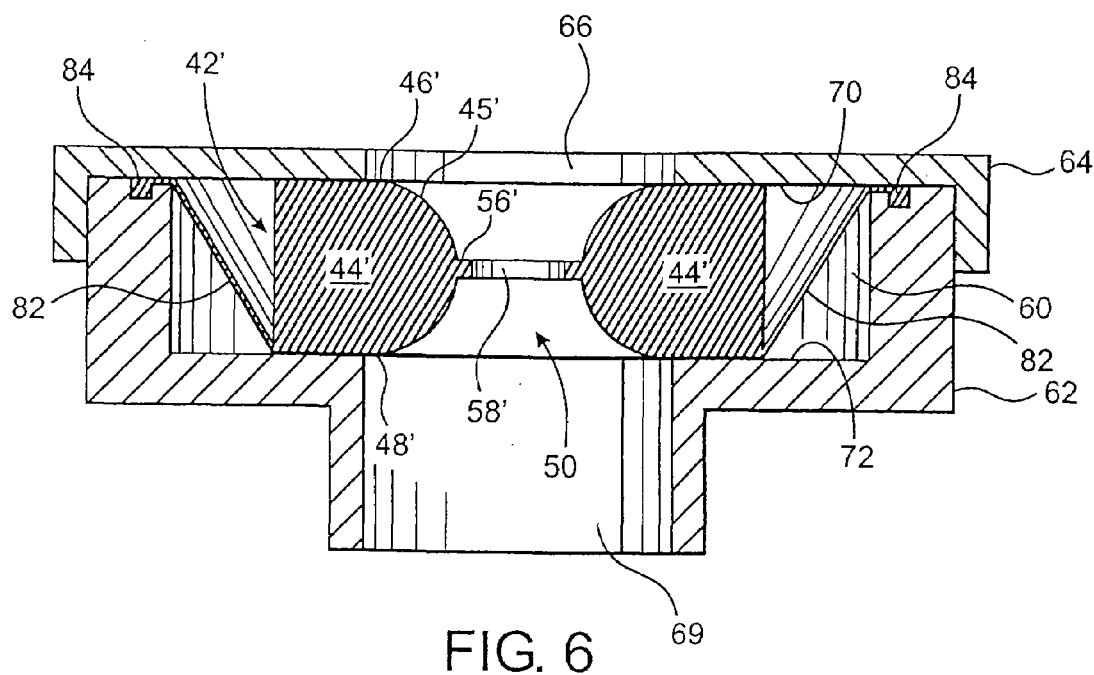
FIG. 6 is a schematic, cross-sectional view of yet another embodiment of the seal assembly of the present invention shown in an assembled, operative position.
Figure 7:
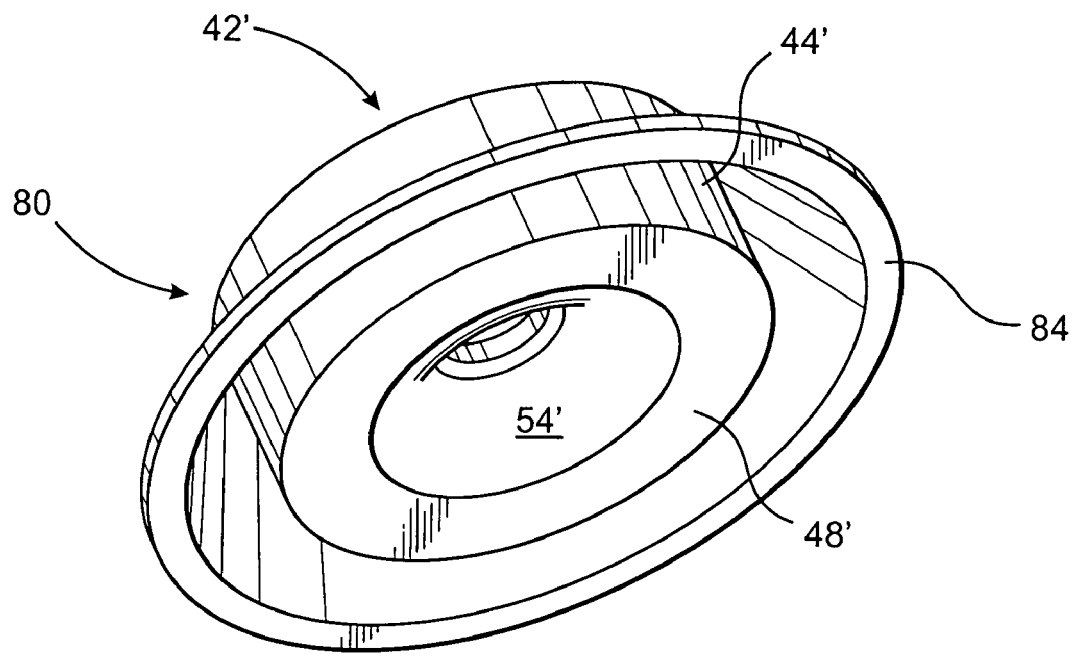
FIG. 7 is a bottom perspective view of the seal member in the embodiment shown in FIG. 6.
Figure 8:
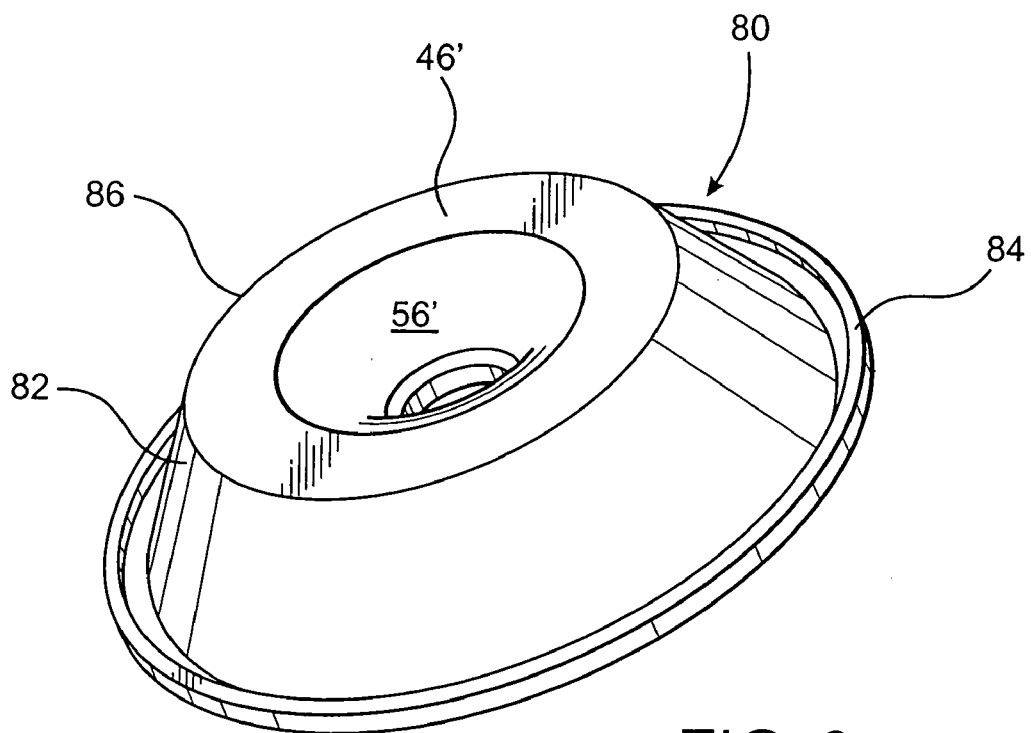
FIG. 8 is a top perspective view of the embodiment of the seal member of FIG. 7.

As noted previously herein, one feature of the present invention is the ability of the seal member 42 to freely move within the chamber 60 due to its not being connected or attached to any structure within the chamber 60, seal housing 62 or sealing closure 64. However, referring now to FIGS. 6 through 8, there is shown another possible embodiment for the present invention, which includes the provision of a positioning means, generally indicated as 80. The positioning means 80 comprises an elastic material skirt or like structure 82 having an enlarged or reinforced outer peripheral rim 84. The inner end of the skirt 82, as at 86, is integrally formed to the outer periphery of one of the first and second outer surfaces, such as at 46'. The skirt 82 is made from an elastic material and is of a relatively thin transverse dimension such that the elasticity or ability to stretch is greater than at least a majority of the body 44'. In its operative position, as shown in FIG. 6, the outer rim 84 is mounted or otherwise secured to the seal housing 62 and/or the under portion of the seal closure 64. As such, the disposition and structure of the positioning assembly 80 is such as to normally orient the seal member 42' in a substantially aligned relation with the inlet port 66 of the seal closure 64. However, due to the elasticity of the surrounding skirt 82 of the positioning assembly 80, the seal member 44' is allowed to freely move or "float" at least laterally within the chamber 60 such as when the interior surface of the body 44' engages the distal end of the instrument being introduced through the inlet port 66. Therefore, it should be understood that the structural and operative features of the seal member 42' render it substantially equivalent to the seal member 42 of the preferred embodiment(s) illustrated previously with respect to FIGS. 2 through 5.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A seal assembly for use with a trocar or like device structured to introduce a medical instrument into a body cavity, said seal assembly comprising:
   a) a seal housing including an interior chamber having an inlet port and an outlet port,
   b) said chamber comprising oppositely positioned inner surfaces each disposed contiguous to a different one of said inlet port and said outlet port and extending radially outward therefrom,
   c) a seal member including a channel extending therethrough, said seal member disposed within said interior chamber and further including a first outer surface and a second outer surface extending radially outward from said channel,
   d) said seal member dimensioned and structured for free, lateral movement within said chamber and disposable into and out of coaxial alignment between said channel and said inlet and outlet ports,
   e) said first and second outer surfaces disposed in movable, sealing engagement with correspondingly positioned ones of said inner surfaces during said lateral movement of said seal member within said interior chamber, and
   f) a sealing flange integrally and continuously formed about an outer periphery of said seal member, and extending angularly outwardly from a corresponding one of said first and second outer surfaces into movable, sealing engagement with correspondingly disposed ones of said inner surfaces of said chamber.

2. A seal assembly as recited in claim 1 wherein said seal member is freely movable within said chamber in an unconnected relation to said seal housing.

3. A seal assembly as recited in claim 1 wherein each of said first and second outer surfaces include a sufficient diametrical dimension to dispose at least a periphery of said seal member in movable, surrounding relation to corresponding ones of said inlet port and said outlet port.

4. A seal assembly for use with a trocar or like device structured to introduce a medical instrument into a body cavity, said seal assembly comprising:
   a) a seal housing including an interior chamber having an inlet port and an outlet port,
   b) said chamber comprising oppositely positioned inner surfaces each disposed contiguous to a different one of said inlet port and said outlet port and extending radially outward therefrom,
   c) a seal member including a channel extending therethrough, said seal member disposed within said interior chamber and further including a first outer surface and a second outer surface extending radially outward from said channel,
   d) said seal member dimensioned and structured for free, lateral movement within said chamber and disposable into and out of coaxial alignment between said channel and said inlet and outlet ports,
   e) said seal member being freely movable within said chamber in an unconnected relation to said seal housing; and
   f) said first and second outer surfaces of said seal member each including a sealing flange integrally and continuously formed about an outer periphery thereof, with each of said sealing flanges extending angularly outwardly at an incline from a respective one of said first and second outer surfaces.

5. A seal assembly as recited in claim 4 wherein said seal member comprises an integral one piece construction.

6. A seal assembly as recited in claim 4 wherein said seal member is structured to include a predetermined-amount of lubricity.

7. A seal assembly as recited in claim 6 wherein said seal member includes a lubricating coating.

8. A seal assembly as recited in claim 4 wherein said sealing flange comprises an annular configuration and extends continuously about the outer periphery of said first and second outer surfaces.

9. A seal assembly as recited in claim 4 wherein each of said sealing flanges is dimensioned and structured to demonstrate a greater degree of elasticity than at least a majority of said base.

10. A seal assembly as recited in claim 4 wherein said channel comprises oppositely disposed open ends each disposed contiguous to a corresponding one of said first and second outer surfaces, each of said open ends configured to facilitate introduction of an instrument therethrough into an interior of said channel.

11. A seal assembly as recited in claim 10 wherein each of said open ends comprises a substantially flared configuration extending divergently outward from said interior of said channel towards a corresponding one of said first or second outer surfaces.

12. A seal assembly as recited in claim 4 further comprising a web structure formed on an interior of said channel and including an aperture extending there through in axial alignment with said channel.

13. A seal assembly as recited in claim 12 wherein said web structure is integrally formed on said interior surface and extends radially inward in surrounding relation to said aperture.

14. A seal assembly as recited in claim 13 wherein said web structure is dimensioned and disposed to facilitate sealing engagement with an instrument passing through said channel and having a diametrical dimension less than or equal to said channel.

15. A seal assembly as recited in claim 4 further comprising a layer of less flexible skin formed on at least part of said first outer surface and said interior surface.

* * * * *